(12) United States Patent
Kasuya

(10) Patent No.: US 7,248,666 B2
(45) Date of Patent: Jul. 24, 2007

(54) X-RAY COMPUTED TOMOGRAPHY APPARATUS

(75) Inventor: Yuichi Kasuya, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 253 days.

(21) Appl. No.: 11/134,353

(22) Filed: May 23, 2005

(65) Prior Publication Data

US 2005/0259782 A1 Nov. 24, 2005

(30) Foreign Application Priority Data

May 24, 2004 (JP) .............................. 2004-153112

(51) Int. Cl.
*A61B 6/00* (2006.01)
(52) U.S. Cl. ........................... 378/15; 378/20; 378/207
(58) Field of Classification Search ............... 378/4–21, 378/193, 195–197, 208–210; 250/370.08, 250/370.09
See application file for complete search history.

(56) References Cited

FOREIGN PATENT DOCUMENTS

| JP | 5-91995 | 4/1993 |
|---|---|---|
| JP | 5-305075 | 11/1993 |
| JP | 8-280661 | 10/1996 |
| JP | 2002-112995 | 4/2002 |
| JP | 2002-345802 | 12/2002 |
| JP | 2003-52689 | 2/2003 |
| JP | 2003-126083 | 5/2003 |

*Primary Examiner*—Courtney Thomas
(74) *Attorney, Agent, or Firm*—Oblon, Spivak, McClelland, Maier & Neustadt, P.C.

(57) ABSTRACT

An X-ray computed tomography apparatus includes a substantially annular frame, a mechanism configured to support rotatably the frame, an X-ray tube mounted on the frame, an X-ray detector mounted on the frame, a position detecting unit configured to detect that the frame passes a reference position, a counting unit configured to count the cumulative number of revolutions of the frame on the basis of an output from the position detecting unit, and a storage unit configured to store data of the cumulative number of revolutions of the frame.

15 Claims, 9 Drawing Sheets

X-RAY COMPUTED TOMOGRAPHY APPARATUS

CROSS-REFERENCE TO RELATED APPLICATIONS

This application is based upon and claims the benefit of priority from prior Japanese Patent Application No. 2004-153112, filed May 24, 2004, the entire contents of which are incorporated herein by reference.

BACKGROUND OF THE INVENTION

1. Field of the Invention

The present invention relates to an X-ray computed tomography apparatus of a type in which an X-ray tube rotate around a subject to be examined.

2. Description of the Related Art

Conventionally, an X-ray computed tomography apparatus has been widely used to take a tomographic image of a subject to be examined. The mainstream of current X-ray computed tomography apparatuses is a type in which an X-ray tube and X-ray detector continuously rotate around a subject to be examined.

A gantry incorporates a motor which rotates/drives an annular rotating frame (support) on which an X-ray tube and X-ray detector are mounted. With this arrangement, the X-ray tube and X-ray detector serve to detect transmitted X-rays while applying X-rays to a subject to be examined from various directions, and the X-ray computed tomography apparatus reconstructs a tomographic image of the subject on the basis of the detected data. The gantry is provided inside with a slip ring and brush for, for example, supplying power to the X-ray tube, the X-ray detector, and the like which rotate, and extracting various kinds of signals (see, for example, Jpn. Pat. Appln. KOKAI Publication No. 8-280661), a bearing (see, for example, Jpn. Pat. Appln. KOKAI Publication No. 5-305075), a pulley and belt for transmitting the power generated by the motor (see, for example, Jpn. Pat. Appln. KOKAI Publication No. 2002-112995), and the like.

In general, the gantry is provided with a tilting mechanism which tilts the frame so as to change the slice angle of scan with respect to a subject to be examined (see, for example, Jpn. Pat. Appln. KOKAI Publication No. 2003-52689). This tilting mechanism comprises a monitor, rollers, sprockets, chains, and the like as disclosed in, for example, Jpn. Pat. Appln. KOKAI Publication No. 5-91995.

A couch is provided with a driving means for driving a top in the vertical and horizontal directions, as disclosed in, for example, Jpn. Pat. Appln. KOKAI Publication No. 2003-126083. The power generated by this driving means is transmitted to the top through pulleys, belts, and the like.

As described above, various kinds of consumable parts and parts that require cleaning, such as slip rings, brushes, bearings, pulleys, belts, rollers, sprockets, and chains, are used for an X-ray computed tomography apparatus. In order to maintain the apparatus in a proper state, it is important to perform maintenance such as cleaning and inspection of the apparatus and replacement of consumable parts at proper timings.

The maintenance of an X-ray computed tomography apparatus has often been performed in a cleaning cycle, inspection cycle, and part replacement cycle set on the basis of reference data created by a maker or the like. In this case, reference data is data concerning the durability of parts and the like, which is created by a maker or the like for, for example, the calculation of the lifetime of an apparatus. This reference data is generally created on the basis of an inspection method unique to each maker, load values, and the like. Such inspection methods have not been unified. For example, in some cases, inspection is done by applying an actual load to an apparatus after a target part is built in it. In other cases, inspection is done while a given standard load value is applied to an apparatus.

According to such a conventional maintenance service, maintenance is performed in a uniform cycle in every hospital regardless of the frequency of use of an X-ray computed tomography apparatus in the hospital. Therefore, the following problems may arise. With regard to an X-ray computed tomography apparatus with a high frequency of use, since a given part greatly wears out in the same period, a proper maintenance timing may be lost. If the apparatus fails due to this, it cannot be used during a repair period. This causes inconvenience to the user. With regard to an X-ray computed tomography apparatus with a low frequency of use, since a given part wears out little in the same period, maintenance may be done before a proper maintenance timing, inflicting unnecessary cost on the user.

As described above, a maintenance timing has been set on the basis of the use period of an X-ray computed tomography apparatus. However, a maintenance timing should be determined on the basis of the frequency of use of the apparatus and, more specifically, the actual operation amount of each part constituting a driving portion. For conventional X-ray computed tomography apparatuses, however, maintenance timings could not be determined on the basis of such a criterion.

In addition, in consideration of the fact that many parts used for an X-ray computed tomography apparatus are developed as parts dedicated to the apparatus, the number of parts as samples in a durability test is greatly limited (for example, about one to three) under the present situation. Therefore, the reliability of reference data is not necessarily high. For example, makers and the like have prevented the occurrence of problems in apparatuses by setting relatively short maintenance cycles. In some cases, a technician of an X-ray computed tomography apparatus designates a maintenance timing on the basis of his/her experience at his/her own discretion. The validity of the maintenance timing is inevitably questionable.

Performing maintenance at the timing based on such data with low reliability and validity will lead to the waste of service provision time and labor on the customer engineer side, and will lead to the waste of cost and the risk of apparatus failure on the user side.

BRIEF SUMMARY OF THE INVENTION

It is an object of the present invention to optimize maintenance timings in an X-ray computed tomography apparatus.

According to a first aspect of the present invention, there is provided an X-ray computed tomography apparatus comprising a substantially annular frame, a mechanism configured to support rotatably the frame, an X-ray tube mounted on the frame, an X-ray detector mounted on the frame, a position detecting unit configured to detect that the frame passes a reference position, a counting unit configured to count the cumulative number of revolutions of the frame on the basis of an output from the position detecting unit, and a storage unit configured to store data of the cumulative number of revolutions of the frame.

According to a second aspect of the present invention, there is provided an X-ray computed tomography apparatus comprising a substantially annular frame, a mechanism configured to support rotatably the frame, an X-ray tube mounted on the frame, an X-ray detector mounted on the frame, a pulse generating unit configured to generate a pulse upon rotation of the frame, a counting unit configured to count the cumulative number of pulses, and a storage unit configured to store data of the cumulative number of pulses counted.

According to a third aspect of the present invention, there is provided an X-ray computed tomography apparatus comprising a substantially annular frame, a mechanism configured to support rotatably the frame, an X-ray tube mounted on the frame, an X-ray detector mounted on the frame, a pulse generating unit configured to generate a pulse upon tilting of the frame, a counting unit configured to count the cumulative number of pulses, and a storage unit configured to store data of the cumulative number of pulses counted.

According to a fourth aspect of the present invention, there is provided an X-ray computed tomography apparatus comprising a top configured to support a subject to be examined, a mechanism configured to support the top so as to allow the top to be freely movable in a longitudinal direction, an X-ray tube, an X-ray detector configured to oppose the X-ray tube through the subject, a pulse generating unit configured to generate a pulse upon movement of the top, a counting unit configured to count the cumulative number of pulses, and a storage unit configured to store data of the cumulative number of pulses counted.

According to a fifth aspect of the present invention, there is provided an X-ray computed tomography apparatus comprising a top configured to support a subject to be examined, a mechanism configured to support the top so as to allow the top to be freely movable in a vertical direction, an X-ray tube, an X-ray detector opposed the X-ray tube through the subject, a pulse generating unit configured to generate a pulse upon movement of the top, a counting unit configured to count the cumulative number of pulses, and a storage unit configured to store data of the cumulative number of pulses counted.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An X-ray computed tomography apparatus according to an embodiment of the present invention will be described below with reference to the views of the accompanying drawing. Note that X-ray computed tomography apparatuses include various types of apparatuses, e.g., a rotate/rotate-type apparatus in which an X-ray tube and X-ray detector rotate together around a subject to be examined, and a stationary/rotate-type apparatus in which many detection elements are arrayed in the form of a ring, and only an X-ray tube rotates around a subject to be examined. The present invention can be applied to either type. In this case, the rotate/rotate type, which is currently the mainstream, will be exemplified. In order to reconstruct one-slice tomographic image data, projection data corresponding to one rotation around a subject to be examined, i.e., about 360°, is required, or (180°+view angle) projection data is required in the half scan method. The present invention can be applied to either of these reconstruction schemes. The former scheme will be exemplified here. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and movement of the electron-hole pairs to an electrode, i.e., a photoconductive phenomenon. As an X-ray detection element, either of these schemes can be used. In this case, the former type, i.e., the indirect conversion type, will be exemplified. Recently, with advances toward the commercialization of a so-called multi-tube type X-ray computed tomography apparatus having a plurality of pairs of X-ray tubes and X-ray detectors mounted on a rotating ring, related techniques have been developed. The present invention can be applied to both a conventional single-tube type X-ray computed tomography apparatus and a multi-tube type X-ray computed tomography apparatus. The single-tube type X-ray computed tomography apparatus will be exemplified here.

(Arrangements of X-ray Computed Tomography Apparatus and Its Maintenance System)

(X-ray Computed Tomography Apparatus)

Figure 1:
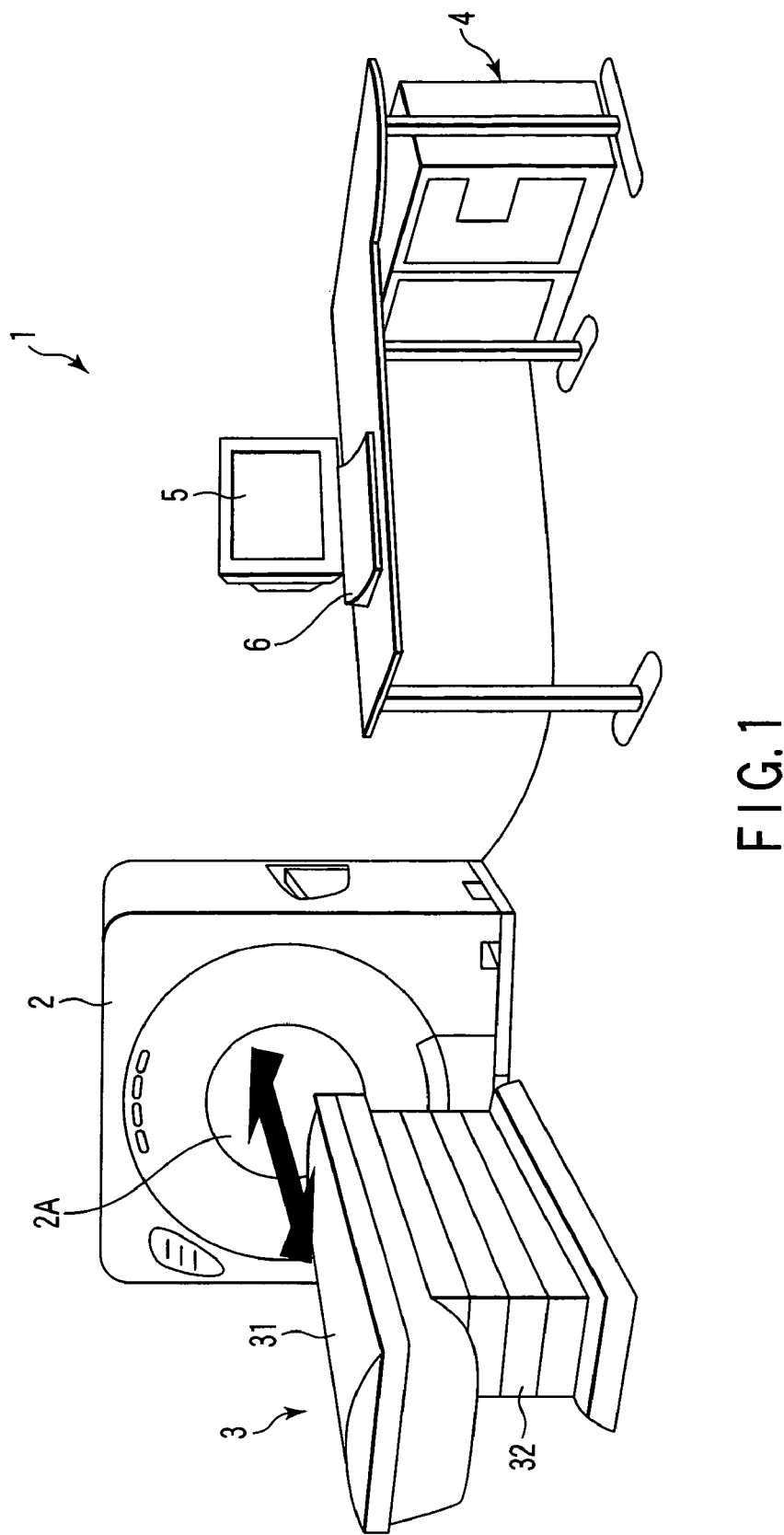
FIG. 1 is a perspective view of an X-ray computed tomography apparatus according to an embodiment of the present invention.

As shown in FIG. 1, an X-ray computed tomography apparatus 1 according to this embodiment has a gantry 2. The gantry 2 has an opening portion 2A. At the time of data acquisition, a subject to be examined is placed in the opening portion 2A by using a couch 3. The couch 3 has a rectangular top 31 and a couch driving unit 32 which supports the top 31 so as to freely drive it in the longitudinal direction and vertical direction. A computer terminal 4 is connected to the gantry 2. The computer terminal 4 controls data acquisition (scanning), tomographic image reconstruction, image display, and the like. A monitor 5 is provided to display a tomographic image, supplementary information, and the like. An input device 6 including a keyboard, a mouse, a trackball, and the like is provided to allow the operator to perform input operation.

Figure 2:
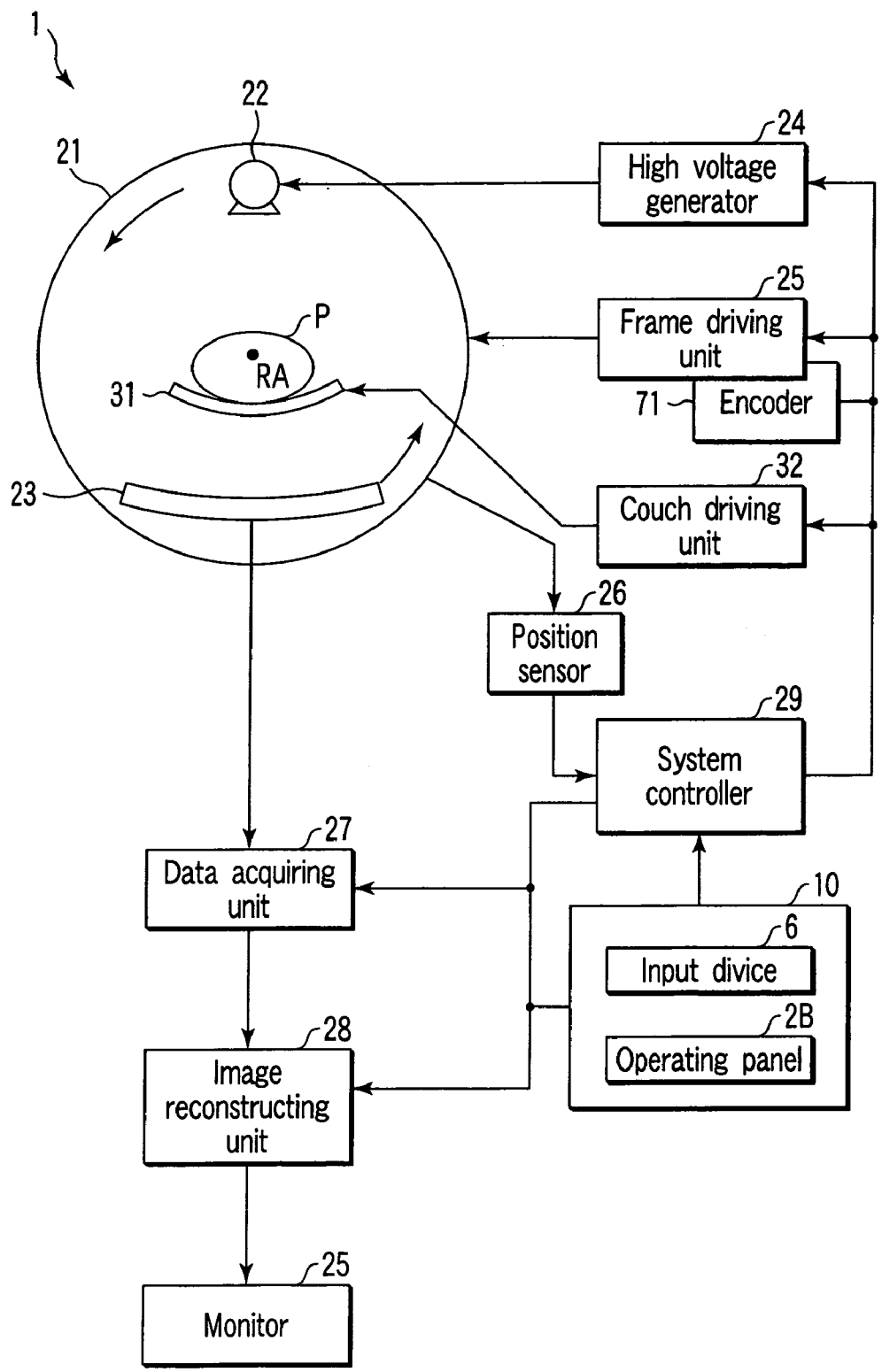
FIG. 2 is a view showing the overall arrangement of the X-ray computed tomography apparatus according to this embodiment.

As shown in FIG. 2, the gantry 2 has a substantially annular rotating frame (frame). A frame driving unit 25 has a mechanism which supports a rotating frame 21 so as to make it freely rotatable around a rotation central axis RA and a motor which generates rotating power. The frame driving unit 25 has a mechanism of supporting the rotating frame 21 so as to make it freely tilt and a motor which generates tilting power. An X-ray tube 22 and X-ray detector 23 are mounted on the rotating frame 21. The X-ray detector 23 opposes the X-ray tube 22 through a subject P to be examined. The X-ray detector 23 detects X-rays transmitted through the subject P. A high voltage generator 24 generates a filament current supplied to the X-ray tube 22, and is provided to generate a tube current to be applied to the X-ray tube 22.

A position sensor 26 detects that the rotating frame 21 passes a reference position, typically the 0° position at the apex, and generates a pulse. As the position sensor 26, for example, an optical sensor unit is used. The optical sensor unit has a light source and a light-receiving unit which are placed on a fixing portion so as to oppose each other. When a light-shielding plate mounted at a specific position on the rotating frame 21 passes through the gap between the light source and the light-receiving unit, an output signal from the light-receiving unit changes. The pulse generating unit of the optical sensor unit detects a change in output signal from the light-receiving unit and generates a pulse.

The position sensor 26 is an existing constituent element for measuring the angle (projection angle) of the X-ray tube 22 in cooperation with an encoder 71 which generates a pulse in accordance with the axial displacement of the motor which generates rotating power. The measured projection angle is coded and associated with projection data.

The transmitted X-ray amount data detected by the X-ray detector 23 is acquired by a data acquiring unit 27. An image reconstructing unit 28 reconstructs a tomographic image on the basis of the projection data acquired by the data acquiring unit 27. The reconstructed tomographic image is displayed on the monitor 5 under the control of the computer terminal 4.

An operation unit 10 is used to perform operation input for designating operation with respect to the gantry 2 and couch 3, and is comprised of the input device 6 forming the above console and an operating panel 2B provided on the housing of the gantry 2. The operator can instruct various kinds of operations such as starting of examination (starting to apply X-rays), rotating or tilting of the rotating frame 21 of the gantry 2, and moving of the top 31 of the couch 3 in the vertical and horizontal directions.

A system controller 29 comprises a CPU and memory provided in the gantry 2, and controls the respective units of the apparatus, e.g., the high voltage generator 24, frame driving unit 25, couch driving unit 32, data acquiring unit 27, and image reconstructing unit 28, in particular, in accordance with programs stored in the memory on the basis of operation contents input by the operator to the operation unit 10, detection results such as the rotational position of the rotating frame 21 obtained by the position sensor 26, and the like. Note that this embodiment may use an arrangement in which the system controller 29 is provided for the computer terminal 4.

Although not shown, the frame driving unit 25 includes parts for rotating and tilting the rotating frame 21, e.g., rotating frame rotating motor for rotating/driving the rotating frame 21, a rotating frame tilting motor for tilting the rotating frame 21, and e.g., bearings, pulleys, belts, rollers, sprockets, and chains, as in the case of the conventional arrangement. The X-ray tube 22 and the like provided on the rotating frame 21 receive power through a spring ring and brush as in the prior art. The X-ray detector 23 and the like output data through the spring ring and brush.

In addition, as in the prior art, the couch driving unit 32 is also comprised of parts, e.g., a top translating motor for translating the top 31, pulleys, belts, a brake, and clutches, a top vertically moving motor for moving the top 31 vertically, a ball screw, an LM (Linear Motion) guide, and parts constituting a driving shaft, e.g., a reduction gear. These parts constituting the frame driving unit 25 and couch driving unit 32 need maintenance (cleaning, inspection, replacement, and the like).

[Maintenance System]

Figure 3:
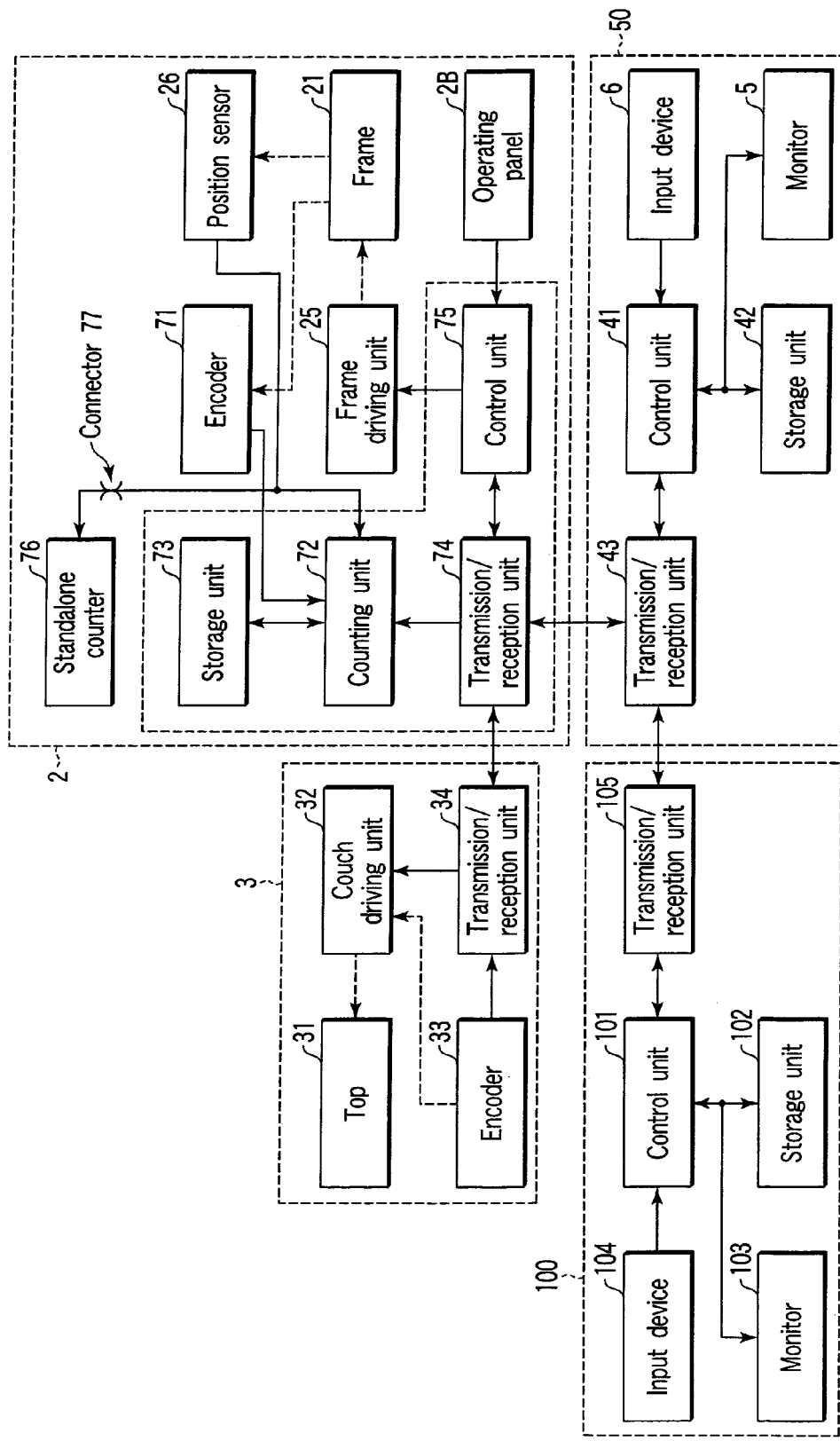
FIG. 3 is a block diagram showing the arrangement of the main part of the X-ray computed tomography apparatus according to this embodiment.

As shown in FIG. 3, the gantry 2, the couch 3, and a console 50 are arranged on the user side, e.g., a hospital. The gantry 2 and the couch 3 are connected to each other through a private line, and so are the gantry 2 and the computer terminal 4 of the console 50.

A server 100 for managing the X-ray computed tomography apparatus 1 is placed on the service provider side which provides a maintenance service for the X-ray computed tomography apparatus 1, and is connected to the console 50 on the user side through a network such as the Internet.

FIG. 3 shows only one X-ray computed tomography apparatus. In practice, however, a plurality of X-ray computed tomography apparatuses to be managed by the server 100 are connected to the server 100.

The gantry 2 is comprised of the rotating frame 21 on which the X-ray tube 22 and X-ray detector 23 are mounted, the frame driving unit 25 for rotating the rotating frame 21, the position sensor 26 which detects that the rotating frame 21 passes the reference position, and generates a pulse, the operating panel 2B for operating the gantry 2 and couch 3, the encoder 71 which generates a pulse in accordance with a predetermined axial displacement of the rotating motor of the frame driving unit 25, a counting unit 72 which counts the number of pulses generated by the position sensor 26 and the number of pulses generated by the encoder 71, a storage unit 73 formed from a nonvolatile storage device which stores the count data obtained by the counting unit 72, a transmission/reception unit 74 which transmits/receives data to/from the couch 3 and console 50, and a control unit 75 which controls the operation of the gantry 2 and couch 3.

As described above, the frame driving unit 25 is provided with the rotating frame rotating motor for rotating the rotating frame 21 and the rotating frame tilting motor for tilting the rotating frame 21. The control unit 75 transmits, to the frame driving unit 25, a control signal representing operation contents (the rotation or tilting of the rotating frame 21) which is input from the operating panel 2B or input device 6. The frame driving unit 25 rotates or tilts the rotating frame 21 by driving the motor designated by a control signal from the control unit 75. In this case, control signals for tilting the rotating frame 21 include a control signal (plus-side tilt signal) for tilting the rotating frame 21 in the positive direction, and a control signal (minus-side tilt signal) for tilting the rotating frame 21 in the negative direction. In addition, as control signals for rotating the rotating frame 21, a plus-side rotating signal for rotating the rotating frame 21 in the positive direction (the direction indicated by the arrows in FIG. 2; the counterclockwise direction), and a minus-side rotating signal for rotating the rotating frame 21 in the negative direction (the clockwise direction) may be selectively used.

The encoder 71 is provided for each motor included in the frame driving unit 25. For example, a motor with an encoder may be used as each of these motors. The encoder 71 generates a pulse signal in accordance with the axial displacement of the corresponding motor. For example, the encoder 71 generates pulse signals by a specified number during one rotation of the driving shaft of the motor.

The number of pulse signals from the encoder 71 which is counted by the counting unit 72 is stored in the storage unit 73 for each motor of the frame driving unit 25. The number of pulse signals from the position sensor 26 which is counted by the counting unit 72 is stored as data representing the number of revolutions of the rotating frame 21 in the storage unit 73. The counting unit 72 increments one by one in accordance with a pulse from the position sensor 26 with the number of revolutions of the rotating frame 21, which is stored in the storage unit 73, being an initial value. With this arrangement, the counting unit 72 counts the cumulative number of revolutions after the number of revolutions is reset.

The number of revolutions stored in the storage unit 73 is reset when the apparatus is installed. The number of revolutions stored in the storage unit 73 is also reset when maintenance is performed.

The number of pulse signals counted may be stored in the storage unit 73 in real time every time counting is ended or at a predetermined timing, e.g., a timing before the system is shut down. The number of pulses counted may also be stored periodically at predetermined intervals (e.g., one-hour intervals).

Note that the counting unit 72, storage unit 73, transmission/reception unit 74, and control unit 75 are formed on a single board. When the counting unit 72, storage unit 73, transmission/reception unit 74, or control unit 75 fails, the board is replaced with a new one. The cumulative number of revolutions and the like stored in the counting unit 72 are reset upon replacement of the board. In order to hold information such as the cumulative number of revolutions, a standalone counter 76 is detachably mounted on the position sensor 26 through a connector 77. The standalone counter 76 comprises a counting unit which cumulatively counts pulses from the position sensor 26, a storage unit which stores the count value, a display unit which displays the count value, a control unit, and a battery. When the board is replaced with a new one, the data in the storage unit 73 is initialized to the count value displayed on the display unit of the standalone counter 76.

The couch 3 has the top 31 on which the subject P is placed and the couch driving unit 32 for moving the top 31 in the vertical and horizontal directions. As described above, the couch driving unit 32 is provided with the top translating motor and top vertically moving motor. Encoders 33 are respectively provided for the translating motor and vertical moving motor. One encoder 33 generates a pulse in accordance with the axial displacement of the translating motor. The other encoder 33 generates a pulse in accordance with the axial displacement of the vertical moving motor. The couch 3 also includes a transmission/reception unit 34 which transmits/receives data to/from the gantry 2.

The control unit 75 transmits a control signal representing the operation content (moving the top 31 in the horizontal or vertical direction) input from the operating panel 2B or input device 6 to the couch driving unit 32 through the transmission/reception units 74 and 34. The couch driving unit 32 moves the top 31 in the horizontal or vertical direction by driving the motor designated by the control signal from the control unit 75. The control signals for translating the top 31 include an inward movement signal for translating the top 31 in the direction to enter the opening portion 2A of the gantry 2, and an outward movement signal for translating the top 31 in the direction to depart from the opening portion 2A. Control signals for moving the top 31 vertically include an upward movement signal for moving the top 31 upward, and a downward movement signal for moving the top 31 downward.

One encoder 33 is provided for each motor of the couch driving unit 32, and generates a pulse signal in accordance with the axial displacement of the corresponding motor. The encoder 33 is designed to generate a pulse every time the top 31 moves by 1 cm. The transmission/reception unit 34 transfers the pulse signal generated by the encoder 33 to the gantry 2. The counting unit 72 of the gantry 2 counts the number of pulses of the pulse signal. The count value is stored in the storage unit 73 at a predetermined timing.

The console 50 is comprised of a control unit 41 comprising the CPU of the computer terminal 4 which controls the console 50 and executes various kinds of computation processing and a memory, a storage unit 42 formed from the hard disk drive of the computer terminal 4 or the like, a transmission/reception unit 43 which transmits/receives data to/from the gantry 2 and server 100, the monitor 5, and the input device 6.

The server 100 is comprised of a control unit 101 comprising a CPU for controlling the server 100 and executing various kinds of computation processing and a memory, a storage unit 102 formed from a hard disk drive or the like, a monitor 103 which displays various kinds of windows, an input device 104 comprising a keyboard, a mouse, a trackball, and the like, and a transmission/reception unit 105 which exchanges data with the console 50.

[Operation of X-Ray Computed Tomography Apparatus]

The operation of the X-ray computed tomography apparatus 1 according to this embodiment having the above arrangement will be described in detail with reference to the flowcharts shown in FIGS. 4 to 7. Note that the processing shown in these flowcharts is configured to store the number of pulse signals counted in real time. However, similar processing is executed even in a case wherein an arrangement with another storage timing is used.

Figure 6:
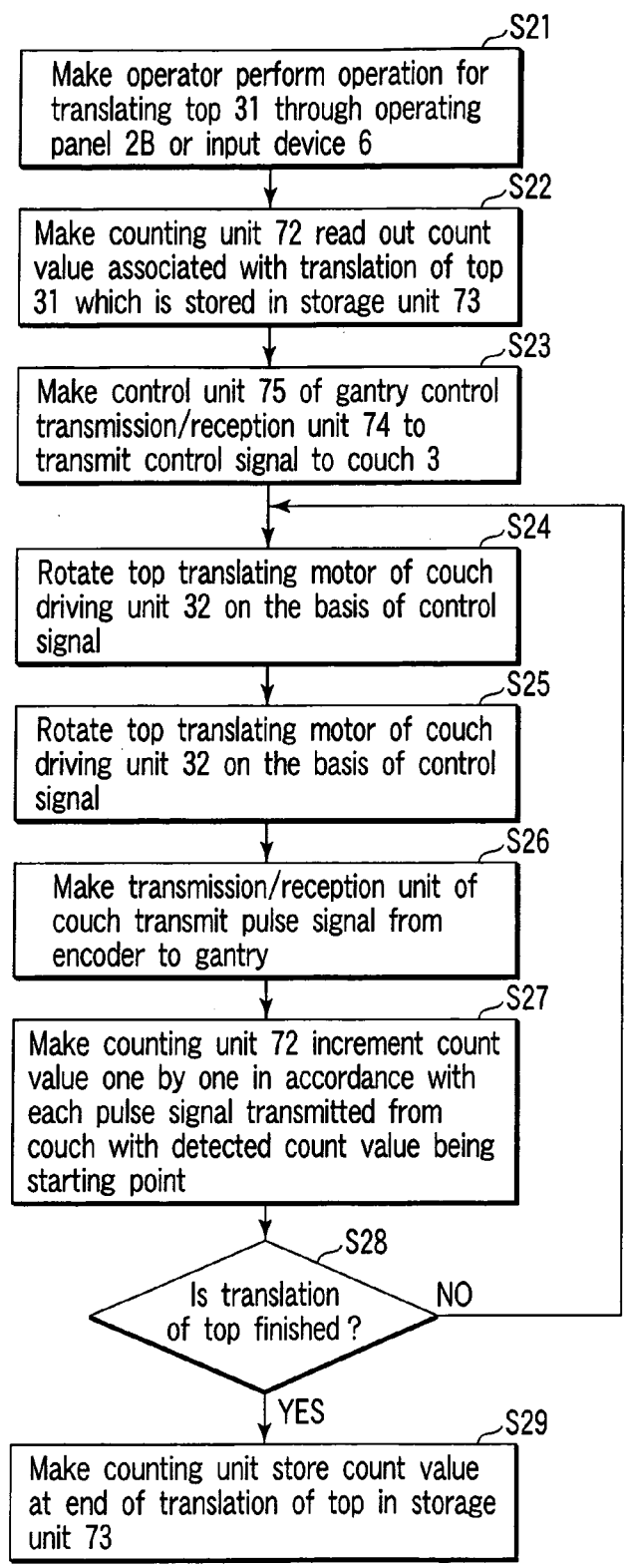
FIG. 6 is a flowchart showing a sequence for counting operation associated with the translation of a top according to this embodiment.
Figure 7:
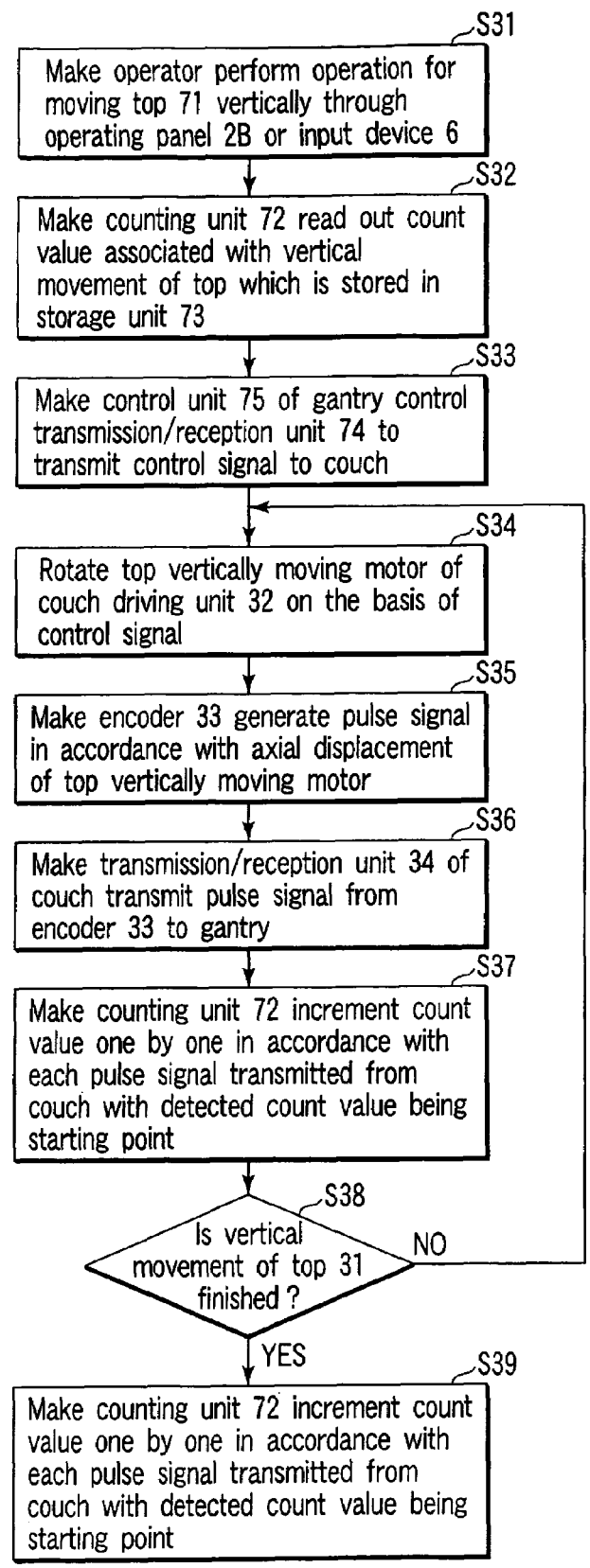
FIG. 7 is a flowchart showing a sequence for counting operation associated with the vertical movement of the top according to this embodiment.

An example of operation in which the X-ray computed tomography apparatus 1 acquires information (the number of revolutions and the number of pulses) about the operation amount of each driving unit in each of the following cases: a case wherein the rotating frame 21 is rotated/driven by the frame driving unit 25 (FIG. 4), a case wherein the rotating frame 21 is tilted by the frame driving unit 25 (FIG. 5), a case wherein the top 31 is translated by the couch driving unit 32 (FIG. 6), and a case wherein the top 31 is moved vertically by the couch driving unit 32 (FIG. 7). In each case, operation executed on the basis of operation by the operator will be described. However, the X-ray computed tomography apparatus 1 executes similar operation even when the rotating frame 21 or top 31 is automatically driven by the system controller 29 in accordance with a program.

In the present invention, "operation amount" includes both the amount by which the frame driving unit 25 or couch driving unit 32 actually operates to drive the rotating frame 21 or top 31 and the amount by which the rotating frame 21 or top 31 is actually operated by the frame driving unit 25 or couch driving unit 32. The former corresponds to the operation time or operation count of the frame driving unit 25 or the like. The latter corresponds to the movement amount or rotational amount of the rotating frame 21 or the like. More specifically, the operation amount based on an operation time corresponds to, for example, the rotating operation time of the motor of the frame driving unit 25 or the like. The operation amount based on an operation count corresponds to, for example, the number of revolutions of the motor of the frame driving unit 25 or the like. The operation amount based on a movement amount corresponds to, for example, the tilt angle of the rotating frame 21 or the horizontal/vertical movement amount of the top 31. The operation amount based on a rotation amount corresponds to, for example, the number of revolutions of the rotating frame 21.

Figure 4:
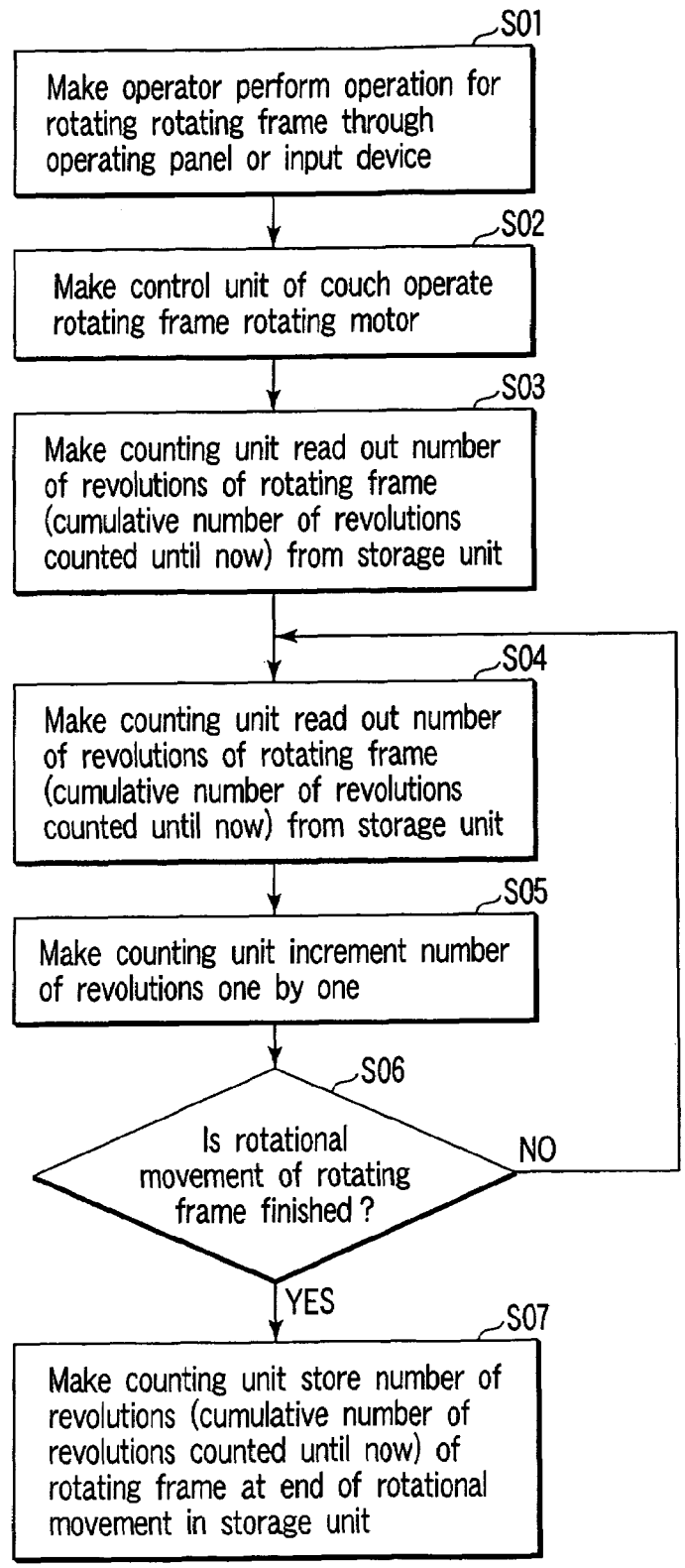
FIG. 4 is a flowchart showing a sequence for counting operation associated with the rotation of a rotating frame according to this embodiment.

[When Rotating Frame Is Rotated/Driven; FIG. 4]

The operation of the X-ray computed tomography apparatus 1 in a case wherein the rotating frame 21 is rotated/driven by the frame driving unit 25 will be described. When the operator performs operation for rotating the rotating frame 21 with the operating panel 2B or input device 6 (S01), the control unit 75 transmits a control signal to the frame driving unit 25 to rotate the rotating frame rotating motor at a predetermined rotational speed (S02). The power generated by the motor is transmitted to the rotating frame 21 through various kinds of parts to rotate the rotating frame 21.

The counting unit 72 reads out the cumulative number of revolutions of the rotating frame 21, counted until now, from the storage unit 73 (S03). The counting unit 72 initializes its count value to the readout number of revolutions.

When the rotating frame 21 passes the reference position, the position sensor 26 generates a pulse (S04). The counting unit 72 increases the number of revolutions one by one in accordance with a pulse from the position sensor 26 (S05). That is, the counting unit 72 counts up the number of revolutions in accordance with a pulse signal from the position sensor 26.

When the rotating frame 21 stops (YES in S06), the counting unit 72 causes the storage unit 73 to store the count value at this time as the cumulative number of revolutions of the rotating frame 21 counted until now (S07). In this case, the detection of the end of the rotational movement of the rotating frame 21 in step S06 is performed on the basis of a control signal corresponding to rotation stopping operation which is supplied from the operating panel 2B or the like.

The number of revolutions stored in the storage unit 73 is displayed on the monitor 5 in accordance with operation through the input device 6 or the like. The corresponding count value may be always displayed on the monitor 5. Furthermore, the upper limit value of the count value may be set in advance so that when the count value reaches the upper limit value, the maintenance timing for parts associated with the rotation of the rotating frame 21 may be notified. As this notification method, for example, a warning window indicating that the maintenance timing has come may be displayed on the monitor 5, or a warning sound may be output from a loudspeaker (not shown). In addition, a date or the like corresponding to the maintenance timing may be displayed. Furthermore, the upper limit value of the count value may be set for each part on the basis of the durability of each part, and a maintenance timing may be notified for each part.

With such operation of the X-ray computed tomography apparatus 1, a count value representing the number of revolutions of the rotating frame 21, i.e., the operation amount information of the rotating frame rotating motor of the frame driving unit 25 and parts which transmit the power generated by the motor, is stored in the storage unit 73, and the operator can be notified of a maintenance timing for the parts associated with the rotation of the rotating frame 21. In this case, the operation amount information (count value) stored in the storage unit 73 is reset (set to "0") on the basis operation through the operating panel 2B, input device 6, or input device 104, or kept stored until being automatically reset by a program. Therefore, the operation amount information of the parts associated with the rotation of the rotating frame 21, obtained after the previous reset operation, is stored in the storage unit 73.

The counting unit 72 has been described as a unit which counts pulses from the position sensor 26. However, the counting unit 72 may count pulses from the encoder 71. In addition, the encoder 71 has been described as a part designed to generate a pulse in accordance with the axial displacement of the motor. However, the encoder 71 may be designed to generate a pulse signal in accordance with the operation time of the motor. For example, the encoder 71 can be designed to generate a pulse signal every time the motor operated for one sec. In this case, the count value of the counting unit 72 represents the operation amount information of a target part on the basis of the operation time of the motor.

In addition, according to the description, the number of revolutions counted by the counting unit 72 is overwritten on the number of revolutions stored in the storage unit 73. However, the number of revolutions may be counted and stored for each examination, daily, weekly, and monthly. The cumulative number of revolutions is calculated by totaling the stored numbers of revolutions.

Figure 5:
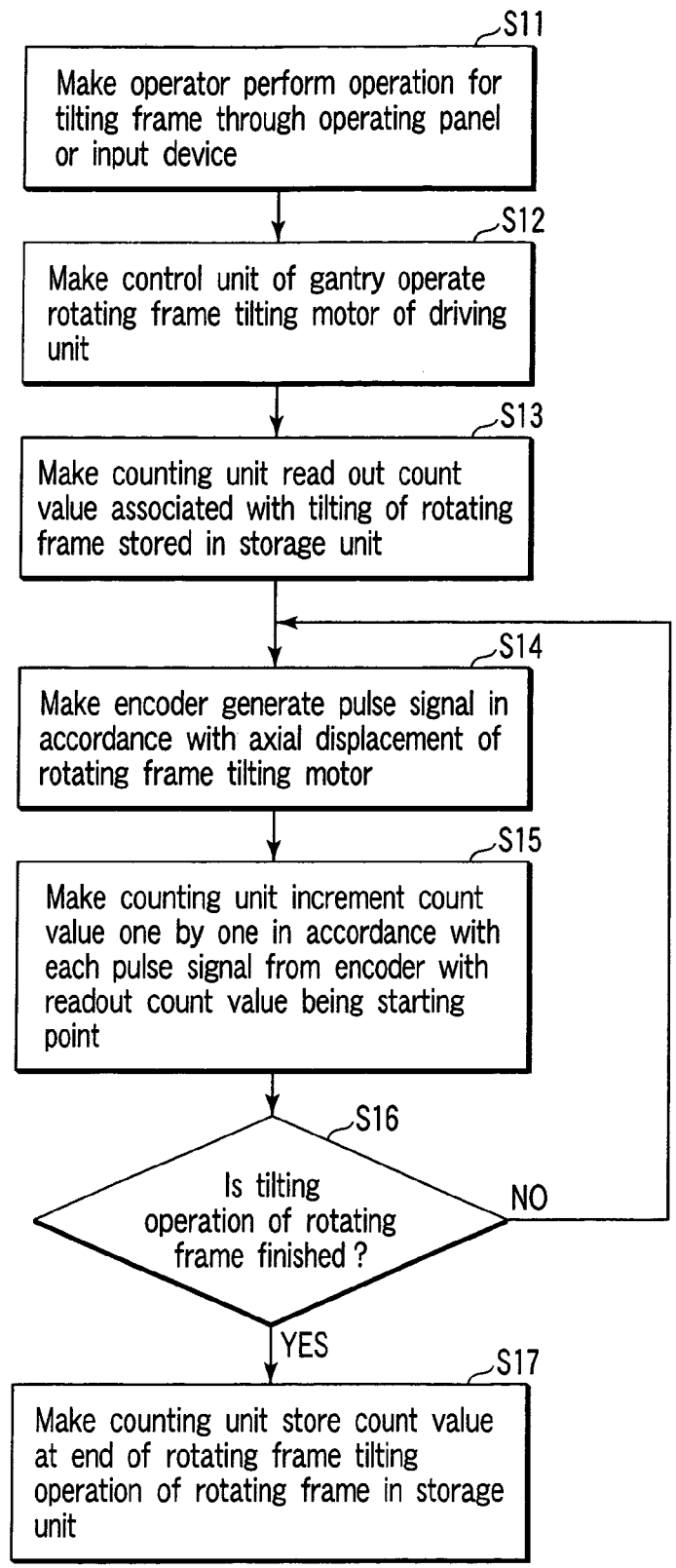
FIG. 5 is a flowchart showing a sequence for counting operation associated with the tilting of the rotating frame according to this embodiment.

[When Rotating Frame Is Tilted; FIG. 5]

The operation of the X-ray computed tomography apparatus 1 in a case wherein the rotating frame 21 is tilted by the frame driving unit 25 will be described. When the operator performs operation to tilt the rotating frame 21 through the operating panel 2B or input device 6 (S11), the control unit 75 transmits a control signal to the frame driving unit 25 to rotate the rotating frame tilting motor at a predetermined rotational speed (S12). The power generated by the motor is transmitted to the rotating frame 21 through various kinds of parts to tilt the rotating frame 21.

The counting unit 72 reads out the cumulative count value counted until now and associated with tilting from the storage unit 73 (S13). The counting unit 72 initializes the count value to the readout count value.

The encoder 71 generates a pulse signal in accordance with the axial displacement of the rotating frame tilting motor of the frame driving unit 25 (S14). In other words, the encoder 71 generates a pulse signal every time the rotating frame 21 tilts at a predetermined angle. In this case, the encoder 71 may generate a pulse signal on the basis of the driving time of the motor, e.g., may generate a pulse signal every second.

The counting unit 72 increments the count value one by one in accordance with a pulse from the encoder 71 (S15). When the tilting operation of the rotating frame 21 is terminated (YES in S16), the counting unit 72 causes the storage unit 73 to store the count value (S17). The stored count value corresponds to the cumulative distance (angle) that the rotating frame 21 has moved in the interval between the time point of the previous reset operation and the end of the current tilting operation. The end of tilting operation in step S16 is detected on the basis of a control signal based on tilting operation finishing operation through the operating panel 2B or the like.

The count value stored in the storage unit 73 is displayed on the monitor 5 on the basis of operation through the input device 6 or the like. The count value may be always displayed on the monitor 5. Furthermore, the upper limit value of the count value may be set in advance, and a maintenance timing for the parts associated with tilting of the rotating frame 21 may be notified when the count value has reached the upper limit value. A notification method for this arrangement is similar to that in the case wherein the rotating frame 21 is rotated/driven.

With this operation of the X-ray computed tomography apparatus 1, a count value indicating how much the rotating frame 21 is tilted, i.e., the operation amount information of the rotating frame tilting motor of the frame driving unit 25 and the parts for transmitting the power generated by the motor, is stored in the storage unit 73, and the operator can be notified of the maintenance timing for the parts associated with tilting of the rotating frame 21. This operation amount information is also stored until the count value is reset by the operator or the like.

The encoder 71 is designed to generate a pulse signal on the basis of the operation time of the rotating frame tilting motor of the frame driving unit 25 (S14). However, the encoder 71 may be designed to generate a pulse signal on the basis of the tilt angle of the rotating frame 21 which is detected by the position sensor 26. For example, the encoder 71 designed to generate a pulse signal every time the rotating frame 21 is tilted by 1° can be used. In addition, for storage processing (S17) of the operation amount information (count value) by the counting unit 72, a processing form similar to that in the case wherein the frame is rotated/driven can be used.

Alternatively, this apparatus may be configured such that pulse signals are generated by using different frequencies and the like in accordance with the rotating direction of the rotating frame tilting motor, i.e., depending on whether the rotating frame 21 is tilted in the positive direction or the negative direction, pulse signals of each type are then independently counted, and the count values are stored. Note that the rotating direction of the motor is detected on the basis of the type of control signal (plus-side rotation signal or minus-side rotation signal) from the control unit 75 or the actual rotating direction of the motor.

[When Top of Couch Is Translated; FIG. 6]

The operation of the X-ray computed tomography apparatus 1 in a case wherein the top 31 is translated in the longitudinal direction by the couch driving unit 32 will be described. The operator performs operation to translate the top 31 through the operating panel 2B or input device 6 (S21).

The counting unit 72 reads out the cumulative count value counted until now and associated with the translation of the top from the storage unit 73 (S22). The counting unit 72 initializes the count value to the readout count value.

The control unit 75 of the gantry 2 controls the transmission/reception unit 74 to transmit a control signal to the couch 3 (S23). The control signal received by the transmission/reception unit 34 of the couch 3 is transmitted to the couch driving unit 32, and the top translating motor is rotated at a predetermined rotational speed on the basis of the control signal (S24). The power generated by the motor is transmitted to the top 31 through various kinds of parts to translate the top 31.

The encoder 33 generates a pulse signal in accordance with the axial displacement of the top translating motor (S25). The transmission/reception unit 34 transmits a pulse signal from the encoder 33 to the gantry 2 (S26).

The pulse signal received by the transmission/reception unit 74 of the gantry 2 is transmitted to the counting unit 72. The counting unit 72 increments the count value one by one in accordance with a pulse from the encoder 33 (S27).

When the translation of the top 31 is finished (YES in S28), the counting unit 72 causes the storage unit 73 to store the count value (S29). The stored count value corresponds to the cumulative distance that the top 31 has moved in the interval between the time point of the previous reset operation and the end of the current tilting operation.

The count value stored in the storage unit 73 is displayed on the monitor 5 on the basis of operation through the input device 6 or the like. The count value may be always displayed on the monitor 5. Furthermore, the upper limit value of the count value may be set in advance, and a maintenance timing for the parts associated with the translation of the top 31 may be notified when the count value has reached the upper limit value. A notification method for this arrangement is similar to that in the case wherein the rotating frame 21 is rotated/driven.

With this operation of the X-ray computed tomography apparatus 1, a count value indicating how much the top 31 is translated, i.e., the operation amount information of the top translating motor of the couch driving unit 32 and the parts for transmitting the power generated by the motor, is stored in the storage unit 73, and the operator can be notified of the maintenance timing for the parts associated with the translation of the top 31. This operation amount information is also stored until the count value is reset by the operator or the like.

Note that the encoder 33 is designed to generate a pulse signal every time the top translating motor of the couch driving unit 32 operates for a unit time (see S24). However, a position sensor which detects the horizontal position of the top 31 may be provided for the couch 3, and a pulse signal may be generated on the basis of a detection signal from the position sensor. In this case, the position sensor is designed to output a detection signal every time the top 31 is translated by, for example, 10 cm, and the operation amount information stored in the storage unit 73 is data representing how many tens of cm the top 31 has been moved in the horizontal direction. In addition, for storage processing (S29) of the operation amount information (count value) by the counting unit 72, a processing form similar to that in the case wherein the frame 21 is rotated/driven or tilted can be used.

Alternatively, this apparatus may be configured such that pulse signals are generated by using different frequencies and the like in accordance with the rotating direction of the top translating motor, i.e., depending on whether the top 31 is moved in the direction to enter the opening portion 2A of the gantry 2 or depart from the opening portion 2A, pulse signals of each type are then independently counted, and the count values are stored. Note that the rotating direction of the motor is detected on the basis of the type of control signal (an inward movement signal or outward movement signal) from the control unit 75 or the actual rotating direction of the motor.

[When Top of Couch Is Moved Vertically; FIG. 7]

The operation of the X-ray computed tomography apparatus 1 in a case wherein the top 31 is moved vertically by the couch driving unit 32 will be described. The operator performs operation for moving the top 31 vertically through the operating panel 2B or input device 6 (S31).

The counting unit 72 reads out the cumulative count value associated with the vertical movement of the top, counted until now, from the storage unit 73 (S32). The counting unit 72 initializes the count value to the readout count value.

The control unit 75 of the gantry 2 controls the transmission/reception unit 74 to transmit a control signal to the couch 3 (S33). The control signal received by the transmission/reception unit 34 of the couch 3 is transmitted to the couch driving unit 32 to rotate the top vertically moving motor at a predetermined rotational speed on the basis of the control signal (S34). The power generated by the motor is transmitted to the top 31 through various kinds of parts to move the top 31 vertically.

The encoder 33 generates a pulse signal in accordance with the axial displacement of the top vertically moving motor (S35). The transmission/reception unit 34 transmits the pulse signal from the encoder 33 to the gantry 2 (S36).

The pulse signal received by the transmission/reception unit 74 of the gantry 2 is transmitted to the counting unit 72. The counting unit 72 increments the count value one by one (S37).

When the vertical movement of the top 31 is finished (YES in S38), the counting unit 72 causes the storage unit 73 to store the count value (S39). The stored count value corresponds to the cumulative distance that the top 31 has moved vertically in the interval between the time point of the previous reset operation and the end of the current tilting operation.

The count value stored in the storage unit 73 is displayed on the monitor 5 on the basis of operation through the input device 6 or the like. The count value may be always displayed on the monitor 5. Alternatively, the upper limit value of the count value may be set in advance, and a maintenance timing for the parts associated with the vertical movement of the top 31 may be notified when the count value has reached the upper limit value. A notification method for this arrangement is similar to that in the case wherein the rotating frame 21 is rotated/driven.

With this operation of the X-ray computed tomography apparatus 1, a count value indicating how much the top 31 has been moved vertically, i.e., the operation amount information of the top vertically moving motor of the couch driving unit 32 and the parts for transmitting the power generated by the motor, is stored in the storage unit 73, and the operator can be notified of the maintenance timing for the parts associated with the vertical movement of the top 31. This operation amount information is also stored until the count value is reset by the operator or the like.

Note that the encoder 33 is designed to generate a pulse signal every time the top vertically moving motor of the couch driving unit 32 operates for a unit time (see S34). However, a position sensor which detects the vertical position of the top 31 may be provided for the couch 3, and a pulse signal may be generated on the basis of a detection signal from the position sensor. In this case, the position sensor is designed to output a detection signal every time the top 31 is moved vertically by, for example, 1 cm, and the operation amount information stored in the storage unit 73 is data representing how many cm the top 31 has been moved in the vertical direction. In addition, for storage processing (S39) of the operation amount information (count value) by the counting unit 72, a processing form similar to that in the case wherein the frame 21 is rotated/driven or tilted can be used.

Alternatively, this apparatus may be configured such that pulse signals are generated by using different frequencies and the like in accordance with the rotating direction of the top vertically moving motor, i.e., depending on whether the top 31 is moved upward or downward, pulse signals of each type are then independently counted, and the count values are stored. Note that the rotating direction of the motor is detected on the basis of the type of control signal (an upward movement signal or downward movement signal) from the control unit 75 or the actual rotating direction of the motor.

[Modification of X-ray Computed Tomography Apparatus]

The X-ray computed tomography apparatus 1 of the above embodiment uses the arrangement in which pulse signals are counted by the counting unit 72 incorporated in the gantry 2. However, pulse signals may be counted by a counter attached to the outside of the gantry 2.

In addition, the number of pulse signals counted is stored in the storage unit 73 incorporated in the gantry 2. However, the number of pulse signals may be stored in a storage medium such as a battery-powered memory with a backup function, a CD-R, or a DVD-RAM.

[Use Form of Maintenance System]

Figure 8:
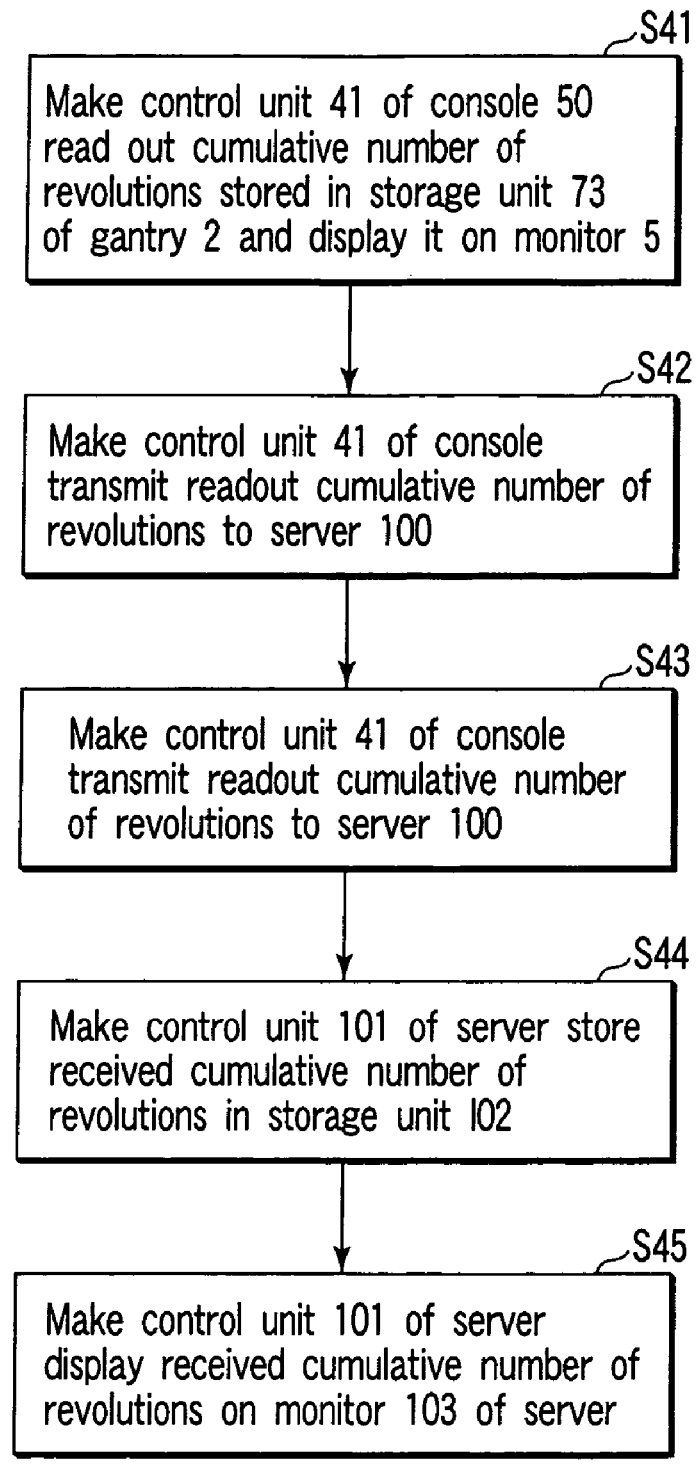
FIG. 8 is a flowchart showing a sequence for display of the cumulative number of revolutions of the rotating frame and transmitting operation according to this embodiment.

FIG. 8 is a flowchart showing a sequence for displaying the cumulative number of revolutions of the rotating frame 21. Display of count values associated with the tilting of the rotating frame 21, the translation of the top 31, and the vertical movement of the top 31 is basically the same as display operation for the cumulative number of revolutions of the rotating frame 21, and hence a description thereof will be omitted.

The control unit 41 of the console 50 reads out the data of the cumulative number of revolutions of the rotating frame 21 from the storage unit 73 of the gantry 2 and displays it on the monitor 5 at power-on, at the end of examination, or periodically (S41). The data of the cumulative number of revolutions of the rotating frame 21 is transmitted to the server 100 through the transmission/reception unit 43 (S42). More specifically, when the control unit 41 transmits a control signal to the gantry 2 through the transmission/reception unit 43, the control unit 75 of the gantry 2 reads out the data of the cumulative number of revolutions stored in the storage unit 73 on the basis of the control signal, and transmits it to the console 50 through the transmission/reception unit 74. The control unit 41 of the console 50 controls the transmission/reception unit 34 to transmit the data of the cumulative number of revolutions to the server 100.

Assume that an upper limit value is set for the count value. In this case, when the count value stored in the storage unit 73 reaches the upper limit value, the data of the cumulative number of revolutions may be transmitted to the server 100. In this case, for example, the control unit 75 (or control unit 41) compares the actual count value with the upper limit value. If the count value exceeds, for example, 90% of the upper limit value, the operation amount information may be transmitted from the console 50 to the server 100.

When the transmission/reception unit 105 of the server 100 receives the data of the cumulative number of revolutions transmitted from the console 50 in step S42 (S43), the control unit 101 stores the data of the cumulative number of revolutions in the storage unit 102 (S44), and displays it on the monitor 103 (S45). In this case, the cumulative number of revolutions received in step S43 may be automatically displayed on the monitor 103, or may be displayed when the operator operates the input device 104 to issue a display request.

According to the first use form of such a maintenance system, the maintenance service provider can grasp the cumulative number of revolutions and the like in the X-ray computed tomography apparatus without visiting a hospital or the like where the X-ray computed tomography apparatus is installed. This makes it possible to save the waste of time and labor. On the user side, this can avoid the waste of cost for excessive maintenance and damage caused by apparatus failure due to a delay of maintenance. In addition, the customer engineer can always grasp the cumulative number of revolutions and the like of the X-ray computed tomography apparatus, and hence can perform maintenance at a proper timing for each X-ray computed tomography apparatus. Furthermore, when a customer engineer is in charge of a plurality of X-ray computed tomography apparatuses, he/she can easily make maintenance schedules for the apparatuses. As described above, according to this maintenance system, remote maintenance for an X-ray computed tomography apparatus can be properly performed.

By acquiring and analyzing pieces of information about a plurality of X-ray computed tomography apparatuses under the control of the server 100, including the cumulative numbers of revolutions and the actual wearout degrees of parts, and the like, the practical service times of parts, the tendency of failures, and the like can be derived. In addition, feeding back the derivation result to the setting of a maintenance cycle and the like makes it possible to perform maintenance at a more proper timing.

Figure 9:
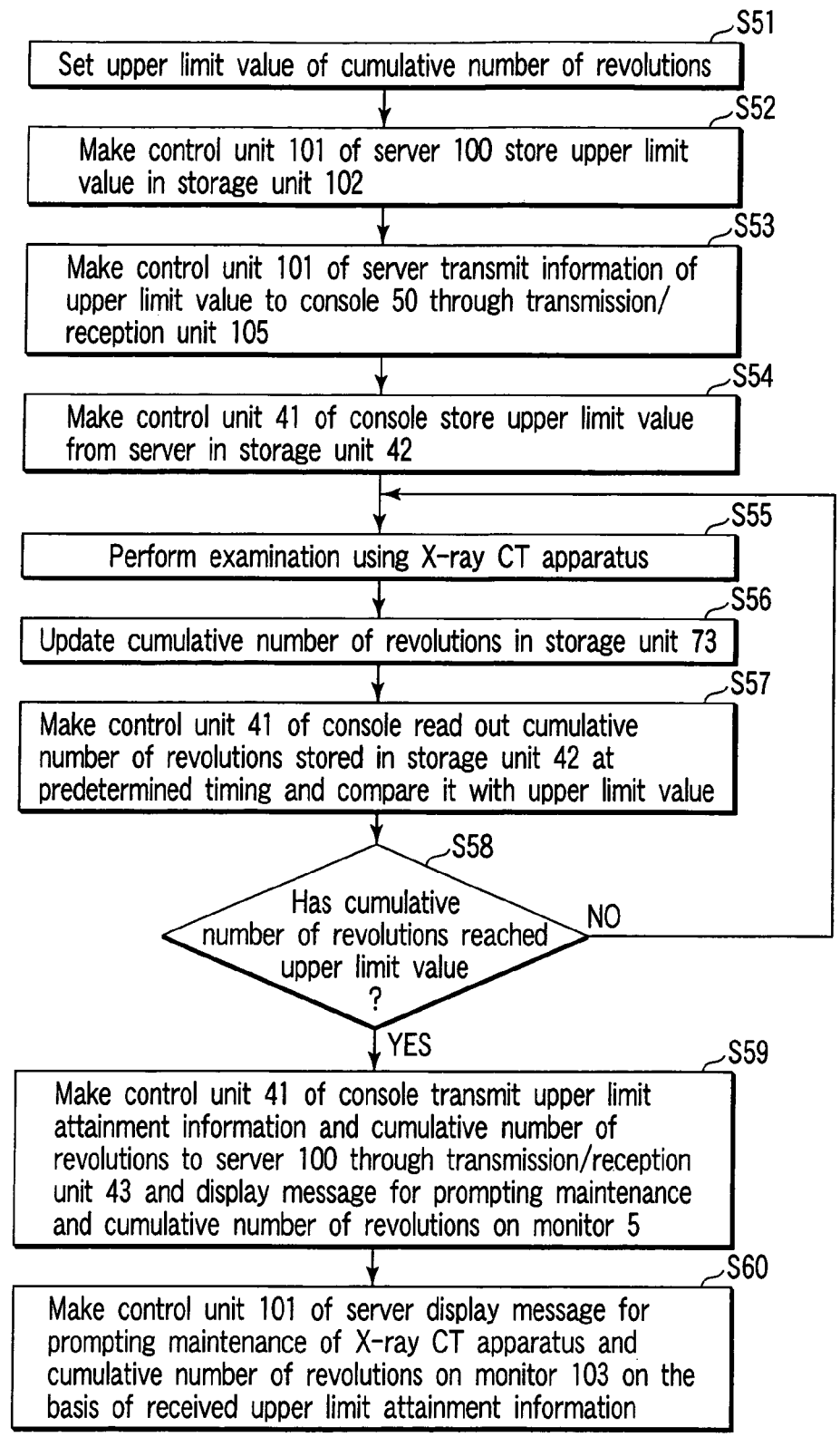
FIG. 9 is a flowchart showing a sequence for management operation of the cumulative number of revolutions of the rotating frame according to this embodiment.

FIG. 9 shows a sequence for managing the cumulative number of revolutions of the rotating frame 21. First of all, an upper limit value is set for the cumulative number of revolutions of the rotating frame 21 in accordance with the durability or the like of parts through the server 100 (or console 50) (S51). The above upper limit value is set in consideration of the maintenance timing for the X-ray computed tomography apparatus. A relatively low upper limit value is set in consideration of the time difference until a maintenance person visits the installation place of the apparatus to perform maintenance.

The control unit 101 of the server 100 stores the setting information of the upper limit value in the storage unit 102 (S52), and transmits the information to the console 50 through the transmission/reception unit 105 (S53). The control unit 41 of the console 50 stores the upper limit value setting information from the server 100, received by the transmission/reception unit 43, in the storage unit 42 (S54).

When examination (scanning) is performed by the X-ray computed tomography apparatus 1 (S55), the cumulative number of revolutions of the rotating frame 21 is counted by processing like that shown in the flowcharts of FIGS. 4 to 7, and stored in the storage unit 73 (S56). The control unit 41 of the console 50 reads out the count value stored in the storage unit 73 at a predetermined timing (e.g., once per day), and compares it with the upper limit value stored in the storage unit 42 (S57).

When the X-ray computed tomography apparatus 1 is repeatedly used, and the cumulative number of revolutions reaches the upper limit stored in the storage unit 73 (YES in S58), the control unit 41 of the console 50 transmits information (upper limit attainment information) indicating this situation to the server 100 through the transmission/reception unit 34, and displays a message for prompting maintenance and the cumulative number of revolutions on the monitor 5 (S59).

When the transmission/reception unit 105 of the server 100 receives the upper limit value attainment information from the console 50, the control unit 101 displays a message for prompting maintenance on the monitor 103 and the cumulative number of revolutions on the monitor 5 (S60).

As a display form in a window, the monitor 103 displays, for example, the date of a maintenance timing or the arrival of a maintenance timing together with the name of the facility (e.g., the hospital) where the X-ray computed tomography apparatus 1 is installed and its contact address or the name of a portion of the apparatus or the name of a part for which maintenance should be done. When this system uses a window for displaying a list of management information about a plurality of X-ray computed tomography apparatuses, the management information of an X-ray computed tomography apparatus for which a maintenance timing is notified may be displayed in a color different from that of the remaining pieces of information. Alternatively, only the name of a part associated with the notification of a maintenance timing may be displayed in a different color.

In step S60, a maintenance timing for the X-ray computed tomography apparatus 1 may be notified by sound output from a loudspeaker (not shown) instead of or together with window display by the monitor 103.

In addition, in step S51, a plurality of upper limit values may be set for each part. For example, upper limit values can be respectively set for a plurality of kinds of maintenance, e.g., cleaning, inspection, and replacement.

A specific example of such a second use form will be described below. First of all, in the upper limit setting processing in step S51, with regard to count values associated with the rotational driving of the rotating frame 21, for example, upper limit values are respectively set for the parts associated with the rotation of the rotating frame 21 as follows: an upper limit value L1 for the slip ring is set to 10,000, an upper limit value L2 for the brush is set to 5,000, and an upper limit value L3 for the rotating frame rotting motor is set to 15,000. With regard to the tilting of the rotating frame 21 and horizontal and vertical movement of the top 31, an upper limit value of operation amount information is set for each part. These pieces of setting information of upper limit values are stored in the storage unit 102 (S52), and are also transmitted to the console 50 on the user side to be stored in the storage unit 42 (S53, S54).

When examination is performed by using the X-ray computed tomography apparatus 1 and the rotating frame 21 and top 31 are driven (S55), count values are accumulated in accordance with the use state (S56). The control unit 41 of the console 50 compares the cumulative count value with the upper limit value (S57). If the count value associated with the rotation of the rotating frame 21 is represented by L, the count value L is compared with corresponding upper limit values L1, L2, L3, . . . , Ln (part count n). If L<Li with respect to all values i=1, 2, . . . , n (NO in S58), no notification is performed, and the use of the X-ray computed tomography apparatus 1 is continued (S55).

If $L \geq Li$ with respect to given value I=1, 2, . . . , n (YES in S58), for example, if L=11,000≧L1 and L2, the control unit 41 generates upper limit value attainment information indicating that the count value associated with the rotation of the rotating frame 21 has reached the upper limit values L1 and L2, and transmits it to the server 100 (S59). The control unit 101 of the server 100 displays, on the monitor 103, a window indicating maintenance timings for the slip ring and brush corresponding to the upper limits L1 and L2, respectively, on the basis of the upper limit value attainment information (S60). Maintenance timings are notified in the same manner with respect to parts associated with the tilting of the rotating frame 21 and the horizontal and vertical movement of the top 31.

According to the second use form of the maintenance system described above, since the maintenance timing for an X-ray computed tomography apparatus can be known in the service center, the waste of time and labor can be eliminated. In addition, maintenance can be performed at a proper timing, thus allowing proper remote maintenance for the X-ray computed tomography apparatus.

According to the X-ray computed tomography apparatus and its maintenance system according to the present invention, it can be expected that appealing high reliability based on the capability of performing maintenance at proper timings allows users and service providers to use apparatuses with a feeling of security. In addition, this gives a feeling of security to patients who visit the hospitals of users and the like.

The arrangement described in detail above is merely an example of the X-ray computed tomography apparatus and its maintenance system according to the present invention, and can be variously modified within the spirit and scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   a rotating frame;
   a mechanism configured to support rotatably the frame;
   an X-ray tube mounted on the frame;
   an X-ray detector mounted on the frame;
   a position detecting unit configured to detect that the frame passes a reference position;
   a counting unit configured to count the cumulative number of revolutions of the frame on the basis of an output from the position detecting unit; and
   a storage unit configured to store data of the cumulative number of revolutions of the frame.

2. An apparatus according to claim 1, further comprising a display unit configured to display a message for prompting maintenance when the cumulative number of revolutions of the frame reaches a predetermined upper limit value.

3. An apparatus according to claim 1, further comprising a display unit configured to display the cumulative number of revolutions of the frame.

4. An apparatus according to claim 1, further comprising a transmitting unit configured to transmit data of the cumulative number of revolutions of the frame to an external maintenance system when the cumulative number of revolutions of the frame reaches a predetermined upper limit value.

5. An apparatus according to claim 1, further comprising a transmitting unit which transmits data of the cumulative number of revolutions of the frame to an external maintenance system.

6. An apparatus according to claim 1, further comprising a standalone counter which is connected to the position detecting unit through a connector.

7. An X-ray computed tomography apparatus comprising:
   a rotating frame;
   a mechanism configured to support rotatably the frame;
   an X-ray tube mounted on the frame;
   an X-ray detector mounted on the frame;
   a pulse generating unit configured to generate a pulse upon rotation of the frame;
   a counting unit configured to count the cumulative number of pulses; and
   a storage unit configured to store data of the cumulative number of pulses counted.

8. An apparatus according to claim 7, wherein the pulse generating unit comprises an encoder which generates the pulse upon axial displacement of a motor which generates power for rotation of the frame.

9. An apparatus according to claim 7, further comprising a display unit configured to display a message for prompting maintenance when the cumulative number of pulses reaches a predetermined upper limit value.

10. An apparatus according to claim 7, further comprising a display unit configured to display the cumulative number of pulses.

11. An apparatus according to claim 7, further comprising a transmitting unit configured to transmit data of the cumulative number of revolutions of the frame to an external maintenance system when the cumulative number of pulses reaches a predetermined upper limit value.

12. An apparatus according to claim 7, further comprising a transmitting unit configured to transmit data of the cumulative number of pulses to an external maintenance system.

13. An X-ray computed tomography apparatus comprising:
   a rotating frame;
   a mechanism configured to support rotatably the frame;
   an X-ray tube mounted on the frame;
   an X-ray detector mounted on the frame;
   a pulse generating unit configured to generate a pulse upon tilting of the frame;
   a counting unit configured to count the cumulative number of pulses; and
   a storage unit configured to store data of the cumulative number of pulses counted.

14. An X-ray computed tomography apparatus comprising:
   a top configured to support a subject to be examined;
   a mechanism configured to support the top so as to allow the top to be freely movable in a longitudinal direction;
   an X-ray tube;
   an X-ray detector configured to oppose the X-ray tube through the subject;
   a pulse generating unit configured to generate a pulse upon movement of the top;
   a counting unit configured to count the cumulative number of pulses; and
   a storage unit configured to store data of the cumulative number of pulses counted.

15. An X-ray computed tomography apparatus comprising:
   a top configured to support a subject to be examined;
   a mechanism configured to support the top so as to allow the top to be freely movable in a vertical direction;
   an X-ray tube;
   an X-ray detector opposed the X-ray tube through the subject;
   a pulse generating unit configured to generate a pulse upon movement of the top;
   a counting unit configured to count the cumulative number of pulses; and
   a storage unit configured to store data of the cumulative number of pulses counted.

* * * * *